United States Patent
Dillinger et al.

(10) Patent No.: US 8,608,646 B2
(45) Date of Patent: Dec. 17, 2013

(54) ENDOSCOPE SHAFT MADE OF A COMPOSITE TUBE

(75) Inventors: Ilona Sabine Dillinger, Aindling (DE); Manfred Josef Grosshardt, Koenigsbrunn (DE)

(73) Assignee: Invendo Medical GmbH, Kissing (DE)

( * ) Notice: Subject to any disclaimer, the term of this patent is extended or adjusted under 35 U.S.C. 154(b) by 304 days.

(21) Appl. No.: 12/943,480

(22) Filed: Nov. 10, 2010

(65) Prior Publication Data

US 2011/0144433 A1 Jun. 16, 2011

(30) Foreign Application Priority Data

Nov. 11, 2009 (DE) .......................... 10 2009 052 688

(51) Int. Cl.
*A61B 1/00* (2006.01)
*A61M 25/00* (2006.01)
*F16L 11/00* (2006.01)

(52) U.S. Cl.
USPC ........... 600/139; 600/114; 600/128; 600/140; 604/524; 604/526; 138/173; 138/174

(58) Field of Classification Search
USPC ......... 600/104, 106, 127–130, 139–152, 108, 600/114–116; 604/523–527; 606/1; 138/173, 174, 176
See application file for complete search history.

(56) References Cited

U.S. PATENT DOCUMENTS

| | | | |
|---|---|---|---|
| 4,634,432 A * | 1/1987 | Kocak | 604/167.04 |
| 6,358,199 B1 * | 3/2002 | Pauker et al. | 600/114 |
| 2003/0176849 A1 * | 9/2003 | Wendlandt et al. | 604/527 |
| 2004/0193013 A1 * | 9/2004 | Iwasaka et al. | 600/140 |
| 2007/0255105 A1 | 11/2007 | Ochi | |
| 2008/0139887 A1 | 6/2008 | Fitzpatrick | |

FOREIGN PATENT DOCUMENTS

| | | |
|---|---|---|
| DE | 8807415 U1 | 8/1988 |
| DE | 10359719 B3 | 4/2005 |
| DE | 202005004169 U1 | 5/2005 |
| EP | 0913165 A1 | 5/1999 |
| JP | 06189898 A | 7/1994 |
| WO | WO 9415522 A1 | 7/1994 |
| WO | WO 2005068887 A2 | 7/2005 |

OTHER PUBLICATIONS

European Search Report for European Application 10190378.9-2319, Mar. 2, 2011.

* cited by examiner

*Primary Examiner* — Matthew J Kasztejna
*Assistant Examiner* — Ryan Henderson
(74) *Attorney, Agent, or Firm* — AlbertDhand LLP

(57) ABSTRACT

An endoscope shaft made of a composite tube comprises an external tube and an internal tube which is softer and more resilient compared to the external tube as well as a helical spring for stiffening the composite tube. According to the invention, the helical spring in the relaxed state has an outer diameter which is larger than the inner diameter of the internal tube. Furthermore the helical spring is inserted in the internal tube preferably loosely at a spring bias, whereby it is radially pressed against the internal tube.

9 Claims, 2 Drawing Sheets

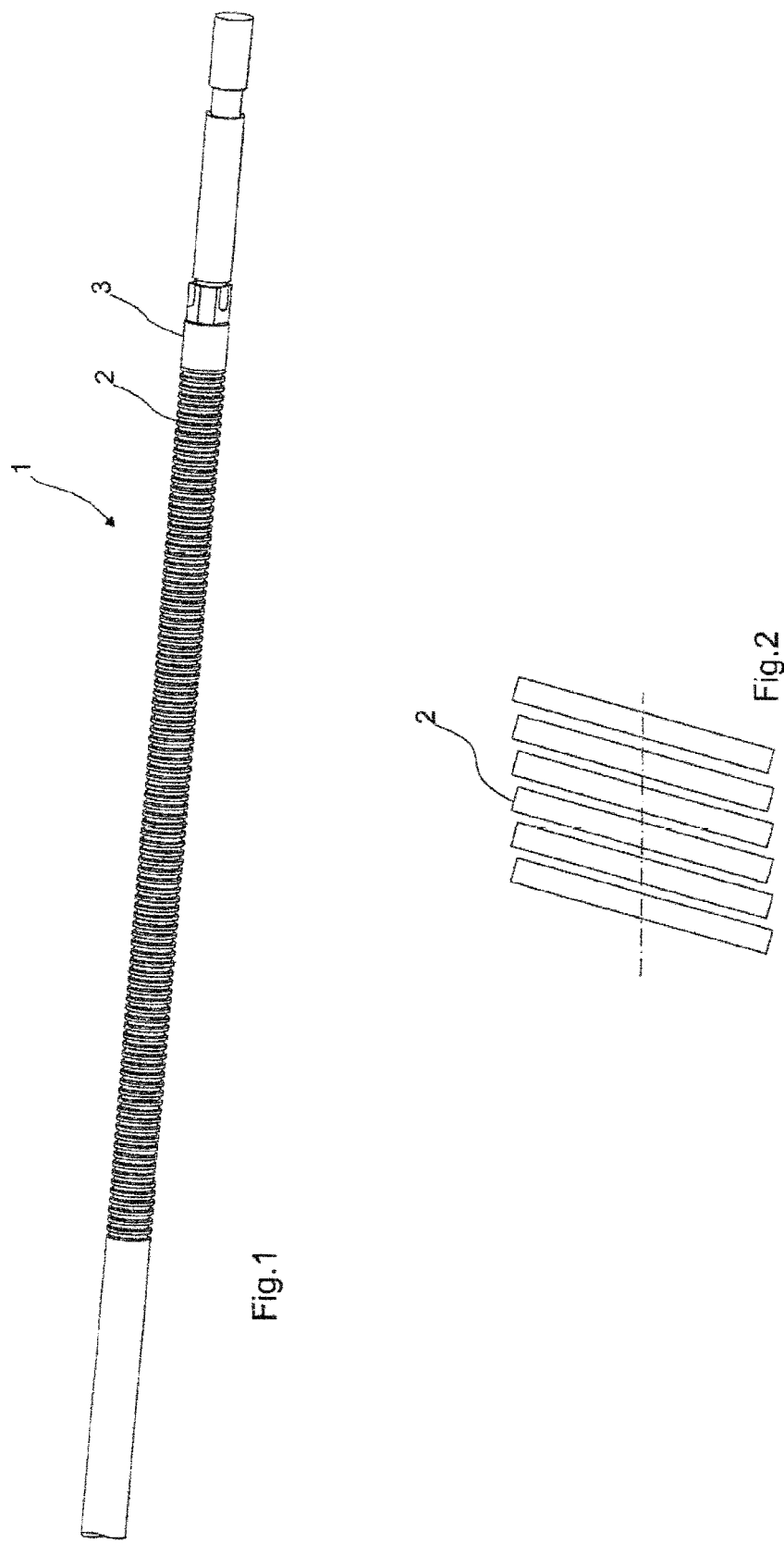

ENDOSCOPE SHAFT MADE OF A COMPOSITE TUBE

The present invention relates to an endoscope shaft made of a composite tube.

Recently, endoscopes have been inserted, for instance, over a considerable distance of up to 2.5 m into the colon of a patient so as to examine and also to treat, if necessary, the latter for pathologic tissue changes such as cancer, polypi, anal fistulae and the like. For overcoming this extremely long inserting distance novel endoscopes are equipped with drive devices, for instance consisting of an everting tube surrounding the endoscope shaft, which in turn can be advanced by means of a drive device and accordingly exerts a feed force upon the endoscope shaft.

From the state of the art, especially of applicant itself, such endoscope comprising an everting tube drive for driving an endoscope shaft forward and backward is known within the scope of a plurality of patent publications. Such endoscope substantially consists of an endoscope shaft which is inserted to slide in an everting tube. The everting tube is formed of a tube of polyvinyl chloride material (PVC) or silicone everted at a distal end and a proximal end of the endoscope shaft (double everting tube design), with a drive device being arranged in the central portion of the tube. The respective ends of the tube everted to the outside are guided back to this drive device and are preferably fixed at the housing of the drive device.

The drive device itself consists either of a continuous advancing mechanism preferably having a number of drive wheels or a crawler or of a discontinuous driving mechanism. Basically the drive device merely drives the everting tube which in turn exerts a drive force upon the endoscope shaft. For this purpose the drive device and the drive mechanism thereof, respectively, are brought in frictional contact with the inner everting tube portion and a feed force is frictionally transmitted to the same. This feed force exerted on the inner portion of the everting tube brings about a respective forward movement of the distal everting portion which gets into contact with a stop fixed at the endoscope shaft and slides off there. Accordingly, the forward movement of the distal everting portion of the everting tube is transmitted via the stop to the endoscope shaft, whereby the latter is entrained inside the inner everting tube portion.

Due to the kinematic conditions, the advance velocity of the inner everting tube portion therefore is twice as high as the advance velocity of the endoscope shaft so that a relative sliding movement is required as a synchronization of movement.

It is obvious from the foregoing description of the state of the art that for transmitting a sufficient feed force to the inner everting tube portion the driving mechanism has to be pressed against the inner everting tube portion with a predetermined minimum contact force. However, this causes a substantially selective indenting of the endoscope shaft in the area of the driving mechanism. Moreover, at this position a higher friction has to be overcome between the endoscope shaft and the inner everting tube portion which is made possible only by sufficient lubrication of the endoscope shaft. Furthermore, it was found that the driving mechanism deforms the endoscope shaft in the short run or in the long run, which results in a non-uniform feed of the everting tube and the endoscope shaft supported in the same.

In order to be able to insert the endoscope into the colon of a patient over the afore-defined distance it is necessary that the endoscope shaft has a high flexibility and resilience. This conflicts with the necessary property of the endoscope shaft, however, to form a sufficiently stiff counter-bearing for the driving mechanism.

In view of these problems, it is the object of the present invention to provide an endoscope shaft made of a composite material which has a sufficient resilience, can be used as counter bearing for the drive device of an everting tube surrounding the endoscope shaft and, moreover, contributes to reducing the friction between the endoscope shaft and the everting tube surrounding the latter.

This object is achieved, according to the invention, by means of an endoscope shaft made of a composite material comprising the features recited in the claims.

Advantageous further developments of the invention are the subject matter of the subclaims.

FIG. 1 is a perspective view of a composite tube according to an embodiment.

FIG. 2 is a schematic representation illustrating rectangular spring geometry of a helical spring according to an embodiment.

Figure 3:
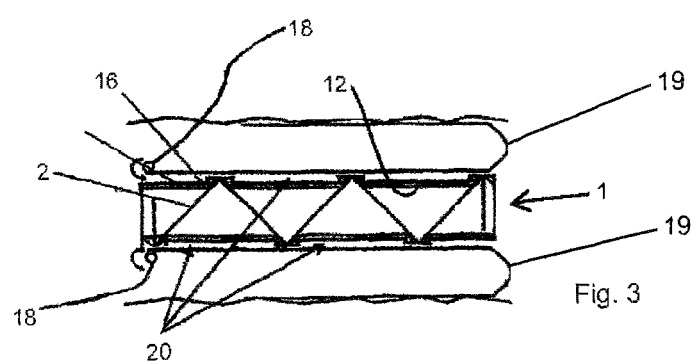
FIG. 3 is a sectional view of a composite tube and portions of a drive device according to an embodiment.

Consequently, the core of the invention consists in manufacturing the endoscope shaft of a composite tube having an external tube and an internal tube softer and/or more resilient compared to the external tube as well as a helical spring for stiffening the composite tube which, according to the invention, in the relaxed state has an outer diameter (slightly) larger than the inner diameter of the internal tube. The helical spring is inserted preferably loosely in the internal tube at a predetermined spring bias (dependent on the spring rigidity as well as the radial oversize), whereby it is radially pressed against the internal tube.

Thus, the helical spring acts as an improved counter bearing for a subsequently disposed drive device for the endoscope shaft not only due to its material stiffness but also due to its mounting at radial bias and in this manner prevents the endoscope shaft from radially deforming due to the pressing forces of the drive device in a lasting manner.

According to another aspect of the present invention, an endoscope shaft is provided comprising an outer tube, the outer circumferential surface thereof has a spiral—like structure. In other words, the outer circumferential surface of the tube forms a rip or protrusion extending in axial direction of the tube in a spiral-like manner.

Here, it is preferably, in that the radially outwardly directed pressing force of the helical spring acting on the internal tube is chosen to be so high that the helical spring according to the first aspect impresses a structure to the outside of the external tube through the walls of the internal tube and the external tube. Further preferably the structure on the outside of the external tube corresponds to the spring windings of the helical spring. This has the advantage that an everting tube which as a drive is arranged to be relatively movable around the endoscope shaft and upon which the drive force of the drive device acts has a reduced contact surface with the endoscope shaft so that the friction between the endoscope shaft and the everting tube can be reduced. Furthermore, the outside structure (surface structure) becoming apparent forms receiving recesses (pockets) in which pressed-in lubricant collects and thus further reduces the friction.

It can be advantageous in this context to design the helical spring to have different spring rigidities and/or gradients and/or outer diameters over the axial length thereof so as to optimize the resilience of the endoscope shaft in portions over the length thereof of preferably 2.5 m.

Consequently, the invention also provides an endoscope comprising such an everting tube drive consisting of a drive tube preferably everted twice which is encompassed by a drive device. The drive device includes drive means (for instance friction wheels) which are in frictional engagement with the drive tube so as to apply a feed force to the drive tube. In accordance with the invention, an endoscope shaft having the foregoing features is provided which is guided to slide in the drive tube and which forms the radial counter bearing for the drive means.

Hereinafter the invention is explained in detail by way of a preferred embodiment with reference to the single accompanying FIGURE. This FIGURE illustrates the side view of an endoscope shaft for an endoscope according to the invention comprising an everting tube drive according to the preferred embodiment of the invention.

Accordingly, the endoscope shaft consists of a composite tube 1 having a so called friction-optimized outer surface. Concretely speaking, the composite tube is formed of two co-extruded or bonded tubes consisting of an internal tube and an external tube, the internal tube being manufactured of a softer material than the external tube. The internal tube ensures minimum flexibility of the composite tube, wherein the external tube ensures minimum resistance to deformation as well as good frictional characteristics at the surface thereof. Concretely speaking, the internal tube has a Shore hardness of approx. 60 Shore A and the external tube has a Shore hardness of approx. 92 Shore A. The internal tube further is preferably manufactured of a PVC material and the external tube is manufactured of a polyurethane (PUR) material.

A helical spring 2 is clamped (injected) into the composite tube 1 for radial stiffening (FIG. 3).

Concretely speaking, the internal tube has an inner diameter which is slightly smaller than the outer diameter of a helical spring 2 in the relaxed state. This helical spring 2 is twisted for the injecting operation whereby the diameter thereof is reduced. Then the helical spring 2 is inserted into the inner diameter of the internal tube 12 over the substantially entire length thereof and is relaxed. Hereby the diameter of the helical spring 2 widens, whereby the helical spring 2 exerts a radial force upon the composite tube 1 resulting in a slight widening of the composite tube 1.

Concretely, the radial pressing force of the inserted helical spring 2 causes the individual spring windings to be seen on the outside of the composite tube 1, thereby a helical rib pattern showing with slight radial bulges and indentations, as illustrated in FIGS. 1 and 3. The spring geometry itself is preferably rectangular, as seen in FIG. 2, so as to most largely exclude tilting of the merely inserted spring 2 for instance by restoring forces of the composite tube 1 or by the pressing forces of a drive device 18 (FIG. 3) of the endoscope equipped with this endoscope shaft. Moreover, the free inner diameter of the composite tube (composite tube and flat spring together) is enlarged by the rectangular spring geometry.

At the proximal end of the composite tube 1, i.e. at the rear end protruding from the body orifice of a patient during operation of the completed endoscope, a lubricating nozzle 3 of a metal piece is arranged on which the composite tube 1 as well as the flat spring 2 are jointly clamped.

As an alternative to the afore-described rectangular spring geometry, it is also possible to design the spring in circular or oval shape. Moreover, there is the option to make use of a spring having two gradients different in the longitudinal spring direction. Hereby the rigidity of the composite tube 1 is influenced as a function of the length thereof. This can be advantageous for optimizing the "travel distance" inside the colon of a patient.

It is another option of optimizing the helical spring used to vary the outer diameter of the spring at steps regularly spaced over the longitudinal direction thereof. This is based on the observation that the helical spring imparts a particular structure to the outside of the composite tube according to the foregoing description which therefore can be formed differently strongly in the longitudinal direction of the composite tube. The advantages for as well as the effects of the endoscope shaft design according to the invention on an endoscope equipped with the latter having an everting tube drive can be summarized as follows:

As explained already in the beginning, an endoscope equipped with the described endoscope shaft comprises an everting tube drive consisting of a tube preferably everted twice which is encompassed by a drive device for a frictional feed force transmission. This drive device brings drive means, for instance drive wheels or a crawler, into frictional contact with a radially inner tube portion so as to drive the same in the longitudinal direction of the everting tube. This drive movement of the inner everting tube portion is transmitted at the front (distal) and/or rear (proximal) everting areas of the everting tube to the endoscope shaft supported to be relatively displaceable inside the everting tube. For the reasons stated in the beginning this relative displacing capability between the endoscope shaft and the inner tube portion of the drive tube is of salient importance.

In order to provide sufficient frictional contact the drive means have to be pressed onto the inner everting tube portion with a particular radial force, wherein for this purpose the inner endoscope shaft serves as counter bearing for the drive means. It is obvious that at this position the friction increases between the endoscope shaft and the inner everting tube portion.

The use of two materials optimized for the function thereof takes this situation into account. That is to say, the soft resilient internal tube ensures a forward movement of the endoscope shaft into the colon of a patient in that the endoscope shaft follows the curvatures of the colon in a resilient manner without excessively widening the same. The external tube which is harder vis-à-vis the internal endoscope shaft tube ensures a predetermined minimum stiffness in radial direction and in this way serves as counter bearing for the drive means of an everting tube drive. It has turned out in this context that the external tube may have a substantially lower wall thickness than the internal tube and still maintains a sufficient radial stiffness.

The helical spring 2 merely (loosely) inserted in the internal tube having a radial oversize vis-à-vis the internal tube causes widening of the entire composite tube 1 and thus impressing of the spring windings at the outside of the external tube, as seen in FIGS. 1 and 3. The helical spring 2 supports the function of counter bearing of the external tube and thus contributes to the fact that the endoscope shaft 1 is not squeezed or radially deformed during its feed by means of the drive device 18 (FIG. 3) in the area of the drive means. The helical spring 2 slightly increases the resilience of the endoscope shaft over the entire length thereof. Finally, as illustrated in FIG. 3, caused by the radial pressing forces of the helical spring 2, the spirally circumferential grooves 20 at the outside of the external tube 16 bring about a reduction of the contact surface between the endoscope shaft 1 and a driving everting tube 19 surrounding the endoscope shaft 1. Due to this reduced support surface, friction forces between the endoscope shaft 1 and the everting tube 19 can be reduced.

Ultimately the grooves 20 form lubricant pockets in which lubricant pressed between the endoscope shaft 1 and the driving everting tube 19 is stored.

The invention claimed is:

1. An endoscope comprising:
   an everting tube drive consisting of a drive tube everted twice which is encompassed by a drive device including drive means which are in frictional engagement with the drive tube so as to apply a feed force to the drive tube; and
   an endoscope shaft which is guided to slide in the drive tube and which forms a radial counter bearing for the drive means, the endoscope shaft comprising a composite tube, the composite tube further comprising an external tube having a wall, an internal tube having a wall and which is at least one of softer and more resilient than the external tube, and a helical spring mounted within the internal tube and adapted to radially press against the internal tube, for stiffening the composite tube;
   wherein the helical spring has windings and an outer diameter such that, in a relaxed state, the outer diameter is larger than an inner diameter of the internal tube, and the helical spring exerts a radially outwardly directed pressing force against a radially inner surface of the internal tube, the radial pressing force being sufficiently high that the helical spring windings impress a structure corresponding to the spring windings, to a radially outer surface of the external tube through the walls of the internal tube and the external tube.

2. The endoscope of claim 1, wherein the helical spring is adapted to the internal tube such that the helical spring embosses a corresponding structure at a radially outer surface of the internal tube due to the radial pressing force elastically applied to the radially inner surface of the internal tube by the helical spring.

3. The endoscope of claim 1, wherein the structure comprises helical elevations and indentations formed on the radially outer surface of the external tube corresponding to spring windings of the helical spring.

4. The endoscope of claim 1, wherein the external tube has a Shore hardness of approximately 92 Shore A and the internal tube has a Shore hardness of approximately S60 Shore A.

5. The endoscope of claim 4, wherein the external tube consists of polyurethane (PUR) material and the internal tube consists of Polyvinyl chloride (PVC) material.

6. The endoscope of claim 1, wherein the external and internal tubes are coextruded.

7. The endoscope of claim 1, wherein the external tube has a wall thickness smaller than that of the internal tube.

8. The endoscope of claim 1, wherein the helical spring exhibits rectangular spring geometry.

9. The endoscope of claim 1, wherein the endoscope shaft length is approximately 2.5 m.

* * * * *